United States Patent
Parker (10) Patent No.: US 8,155,980 B2
(45) Date of Patent: *Apr. 10, 2012

(54) SYSTEMS AND METHODS FOR MANAGING MEDICAL DATA

(75) Inventor: Jason Parker, Raleigh, NC (US)

(73) Assignee: Quintiles Transnational Corp., Durham, NC (US)

( * ) Notice: Subject to any disclaimer, the term of this patent is extended or adjusted under 35 U.S.C. 154(b) by 216 days.

This patent is subject to a terminal disclaimer.

(21) Appl. No.: 12/705,816

(22) Filed: Feb. 15, 2010

(65) Prior Publication Data

US 2010/0262429 A1    Oct. 14, 2010

Related U.S. Application Data

(63) Continuation-in-part of application No. 11/354,062, filed on Feb. 14, 2006, now Pat. No. 7,689,439.

(51) Int. Cl.
*G06Q 50/00* (2012.01)
(52) U.S. Cl. .................... 705/2; 705/3; 600/300
(58) Field of Classification Search ............ 705/2–3
See application file for complete search history.

(56) References Cited

U.S. PATENT DOCUMENTS

| | | | |
|---|---|---|---|
| 4,388,759 A | 6/1983 | Orejola | |
| 4,601,291 A | 7/1986 | Boute et al. | |
| 4,936,022 A | 6/1990 | Grayzel | |
| 5,305,202 A | 4/1994 | Gallant et al. | |
| 5,319,543 A | 6/1994 | Wilhelm | |
| 5,469,858 A | 11/1995 | Osborne | |
| 5,515,176 A | 5/1996 | Galen et al. | |
| 5,549,654 A | 8/1996 | Powell | |
| 5,605,158 A | 2/1997 | Snell | |
| 5,669,391 A | 9/1997 | Williams | |
| 5,701,894 A | 12/1997 | Cherry et al. | |
| 5,724,985 A | 3/1998 | Snell et al. | |
| 5,792,065 A | 8/1998 | Xue et al. | |
| 5,819,741 A | 10/1998 | Karlsson et al. | |
| 5,891,049 A | 4/1999 | Cyrus et al. | |
| 5,903,889 A | 5/1999 | de la Huerga et al. | |
| 5,911,687 A | 6/1999 | Sato et al. | |
| 6,141,584 A | 10/2000 | Rockwell et al. | |
| 6,325,756 B1 | 12/2001 | Webb et al. | |
| 6,463,320 B1 | 10/2002 | Xue et al. | |

(Continued)

FOREIGN PATENT DOCUMENTS

WO    WO 98/50873    11/1998

(Continued)

OTHER PUBLICATIONS

CORDIGITAL™ Telemedical Solutions, Micro12ECG+ Manual (16 pages), at least as of a 1998.

(Continued)

*Primary Examiner* — Gerald J. O'Connor
*Assistant Examiner* — Sind Phongsvirajati
(74) *Attorney, Agent, or Firm* — Kilpatrick Townsend & Stockton LLP (57) ABSTRACT

Managing electrocardiogram (ECG) processing is described. ECGs are distributed to a technician system and/or a cardiologist system based on protocol data and one or more factors to promote processing efficiency for the ECGs. A modification to the protocol data can be received. Processed ECGs can be analyzed in view of the modification to identify ECGs for reprocessing. The identified ECGs can be reprocessed in accordance with the modification to the protocol data and, if applicable, the factors.

19 Claims, 8 Drawing Sheets

U.S. PATENT DOCUMENTS

| | | | |
|---|---|---|---|
| 6,575,901 | B2 | 6/2003 | Stoycos et al. |
| 6,580,817 | B2 | 6/2003 | Badilini |
| 6,603,464 | B1 | 8/2003 | Rabin |
| 6,640,212 | B1 | 10/2003 | Rosse |
| 6,650,932 | B1 | 11/2003 | Menzie et al. |
| 6,708,057 | B2 | 3/2004 | Morganroth |
| 6,804,656 | B1 | 10/2004 | Rosenfeld et al. |
| 6,934,578 | B2 | 8/2005 | Ramseth |
| 7,654,965 | B2 | 2/2010 | Morganroth |
| 2002/0059030 | A1 | 5/2002 | Otworth et al. |
| 2002/0172404 | A1 | 11/2002 | Badilini |
| 2003/0060689 | A1 | 3/2003 | Kohls et al. |
| 2003/0208378 | A1 | 11/2003 | Thangaraj et al. |
| 2004/0006553 | A1 | 1/2004 | De Vries et al. |
| 2004/0051721 | A1 | 3/2004 | Ramseth |
| 2004/0054296 | A1 | 3/2004 | Ramseth |
| 2004/0204910 | A1 | 10/2004 | Brumbach et al. |
| 2006/0161067 | A1 | 7/2006 | Elion |
| 2006/0167367 | A1 | 7/2006 | Stanczak et al. |

FOREIGN PATENT DOCUMENTS

| | | |
|---|---|---|
| WO | WO 00/40145 | 7/2000 |
| WO | WO 02/15818 A2 | 2/2002 |
| WO | WO 03/071391 | 8/2003 |
| WO | WO 2006/086181 | 8/2006 |

OTHER PUBLICATIONS

"Magellan ECG Research Workstation Software Operator's Manual," Software Version 2.0, PN 421681-001 Revision C, GE Marquette Medical Systems, Inc., Jan. 10, 2000.

Marquette® HL7 Interface Professional Toolkit Operator's Manual, Software Version 5A PN 40852-30 Revision D (392 pages), Aug. 9, 1999.

Muse CV® Messaging Installation & Configuration—005A & 005B, GE Marquette (16 pages), Jul. 13, 1999.

Muse CV® Web Server Instruction Guide to Enabling SSL, GE Medical Systems Information Technologies, Muse CV Information System 2003934-001, Revision B (24 pages), Dec. 7, 2001.

Muse CV® Information System Conversions, Forklifts, New Systems, Pre-Quote Survey, Software Version 005C, PN 2002783-029, Revision A, GE Marquette, May 31, 2000.

Physician's Guide to Marquette Electronics Resting ECG Analysis, © Marquette Electronics, Inc., Milwaukee, WI, 1988, 1989, 1990, 1991.

The Card Guard CG-7000DX, 12 Lead ECG Recorder/Transmitter Physician's Guide (22 pages).

TM 2000 Patient Monitoring System, System Requirements Specification, Card Guard Scientific Survival Ltd. Document No. 590043 (46 pages), Jan. 30, 1997.

Bhullar et al., "A Computer Based System for the Study of QT Intervals," Departments of Engineering and Cardiology, University of Leicester, Leicester, UK, IEEE, pp. 533-536, 1992.

Bland, et al., "Statistical Methods for Assessing Agreement Between Two Methods of Clinical Measurement", Department of Clinical Epidemiology and Social Medicine, St. George's Hospital Medical School, London, The Lancet, pp. 307-310, Feb. 8, 1986.

Savelieva, et al., "Agreement and Reproducibility of Automatic Versus Manual Measurement of QT Interval and QT Dispersion," Excerpta Medica, Inc. pp. 471-536,1998.

Lawson et al., "New Method for Digitization and Computerized Analysis of Paper Recordings of Standard 12-Lead Electrocardiograms," IEEE—Computers in Cardiology , pp. 41-44, 1995.

Lepeschkin, M.D. et al., "The Measurement of the Q-T Interval of the Electrocardiogram", From the Division of the Experimental Medicine, University of Vermont College of Medicine and the Bishop De Goesbriand Hospital, Burlington, Vermont Circulation, vol. VI, pp. 378-388, Sep. 1952.

Morganroth, M.D. et al., "How to Obtain and Analyze Electrocardiograms in Clinical Trials: Focus on Issues and Interpreting Changes in the QTc Interval Duration", From the Department of Medicine, University of Pennsylvania, Presented at the University of Pennsylvania Symposium on ECGs in Clinical Drug Development in Philadelphia, Pennsylvania Mar. 30, 1999, pp. 425-433.

Murray et al., "Errors in Manual Measurement of QT Intervals", Br Heart Journal, vol. 71, pp. 386-390, 1994.

Willems et al., "A Reference Data Base for Multilead Electrocardiographic Computer Measurement Programs," J. American College of Cardiology, vol. 10, No. 6, Dec. 1987, pp. 1313-1321.

Willems et al., "Development of a Reference Library for Multi-Lead ECG Measurement Programs," J. Electrocardiology Supplemental Issue Oct. 1987, pp. 56-61.

Willems et al., "Influence of Noise on Wave Boundary Recognition by ECG Measurement Programs," Computers and Biomedical Research, Dec. 20, 1987, pp. 543-562.

Willems, M.D., "CSE Project Leader, Assessment of the Diagnostic Performance of ECG Computer Programs and Cardiologists", Common Standards for Quantitative Electrocardiography, Commission of the European Communities, CSE 10th and Final Progress Report, Dec. 31, 1990, pp. 148-261.

Willems et al., "Common Standards for Quantitative Electrocardiography: The CSE Pilot Study," In: Lecture Notes in Medical Informatics, Lindberg, D.A.B. and Reichertz P.L., eds. New York: Springer Verlag, 11 (1981), pp. 319-326.

Muse CV® Information System, CPU-CPU/DHCP Interface Installation (Versions of 005A, 005B, & 005C), GE Marquette (16 pages), Mar. 31, 2000.

Department of Health and Human Service's, Food and Drug Administration, Electronic Interchange Standard for Digital ECG and Similar Data; Public Meeting, (4 pages), Published Oct. 24, 2001.

Muse Version 5C.04 Release Overview, Jan. 14, 2001 (6 pages).

Three (3) Screen Shots of ECGs Produced by G.E. Muse.

Willems, et al., "The Diagnostic Performance of Computer Programs for the Interpretation of Electrocardiograms," The New England Journal of Medicine vol. 325, No. 25, pp. 1767-1773, Dec. 19, 1991.

The CSE Working Party, "Recommendations for Measurement Standards in Quantitative Electrocardiography," European Heart Journal, (1985) 6, pp. 815-825, 1985, The European Society of Cardiology.

Muse CV® Information System Operator's Manual, Software Version 005B, PN 421619-001, Revision C, GE Marquette (510 pages), Sep. 8, 1999.

Morganroth, et al., "How to Obtain and Analyze Electrocardiograms in Clinical Trials: Focus on Issues in Measuring and Interpreting Changes in the QTc Interval Duration." A.N.E. Oct. 1999, vol. 4, No. 4.

International Search Report/Written Opinion for PCT/US07/004150, mailed Jun. 29, 2007.

International Business Machines Corporation, "Scheme-Based Work Assignment in a Workflow System", Research Disclosure, Oct. 2000.

Non-Final Office Action mailed on May 12, 2009 for U.S. Appl. No. 11/354,062.

Response to Non-Final Office Action filed on Aug. 28, 2009 for U.S. Appl. No. 11/354,062.

Notice of Allowance mailed on Nov. 16, 2009 for U.S. Appl. No. 11/354,062.

Record

- Patient ID and Information 802
- Clinical Test Site ID 804
- ECG Test Information 806
- Destination Information 808
- Origination Information 810
- Error Check/Correction Trail 812
- Biometric Signatures 814
- ECG Measurements 816
- Cardiologist Report 818
- ECG 820
- Flag for Modified Protocol Data 822

Figure 8

SYSTEMS AND METHODS FOR MANAGING MEDICAL DATA

CROSS-REFERENCE TO RELATED APPLICATIONS

This application is a continuation-in-part application of U.S. application Ser. No. 11/354,062, titled "System and Method for Managing Medical Data," and filed Feb. 14, 2006, the entire contents of which is incorporated herein by this reference.

TECHNICAL FIELD

This invention relates generally to systems and methods for managing medical data, and more particularly to managing electrocardiogram data in connection with a clinical trial.

BACKGROUND

Clinical trials are often performed to determine whether and how a drug, a medical procedure, or a treatment affects a particular type of patient or patients in general. Medical data regarding participating patients can be obtained over time during the course of a clinical trial, and analyzed. Various types of medical data of patients can be obtained and analyzed during clinical trials. One type is an electrocardiogram (ECG or EKG). An ECG is a representation of electrical activity over time of a patient's heart.

An ECG can be valuable information that indicates, for example, whether a drug or other medical procedure is affecting a patient's heart function. An ECG can be obtained at a clinical trial test site—which may be a medical provider office that is implementing the clinical trial—but analyzed at a remote location by a cardiologist.

An ECG is often a graphical representation of the electrical activity. Technicians or other personnel can obtain measurements from the graphical representation. Examples of measurements include QT, PR, ST, and RR intervals. A cardiologist can review and analyze the measurements to determine whether a patient's heart may be affected by a drug or other medical procedure. The cardiologist can issue a report that is associated with the patient.

Computer systems can be used to manage clinical trial data acquisition, analysis, and storage. Computer systems can be used to provide an ECG for measurement by a technician using a computer interface and for review by a cardiologist using another computer interface. Computer systems can provide data associated with a protocol such that the ECGs are measured in accordance with the data associated with the protocol. The computer systems can allow the technician, cardiologist, data storage, and clinical trial site to each be in a separate location with respect to each other, and continue to process ECGs. The computer systems can also support electronic submission of ECGs and reports to the clinical trial organizers and to the Federal Drug Administration (FDA) in a format acceptable to the FDA.

Such computer systems may be unable to manage the ECGs among technicians that measure the ECGs and among cardiologists that review the measured ECGS efficiently to meet one or more deadlines associated with the clinical trial, or other clinical trial-related factors. For example, such computer systems may be unable to select intelligently a technician to measure an ECG of a patient or a cardiologist to review the measured ECG. Furthermore, such computer systems may be unable to process ECGs efficiently in view of a modification to data associated with a protocol to, for example, meet one or more deadlines (or other requirements) in accordance with the modification.

Accordingly, systems and methods are desirable that can allow ECGs to be processed efficiently while accounting for a modification to a protocol.

SUMMARY

Certain aspects and embodiments of the present invention relate to managing electrocardiogram (ECG) processing. In some embodiments, ECGs are distributed to a technician system and/or a cardiologist system based on protocol data and one or more factors to promote processing efficiency for the ECGs. A modification to the protocol data can be received. Processed ECGs can be analyzed in view of the modification to identify ECGs for reprocessing. The identified ECGs can be reprocessed in accordance with the modification to the protocol data and, if applicable, the factors.

These illustrative aspects and embodiments are mentioned not to limit or define the invention, but to provide examples to aid understanding of the inventive concepts disclosed in this application. Other aspects, advantages, and features of the present invention will become apparent after review of the entire application.

DETAILED DESCRIPTION

Certain aspects and embodiments of the present invention relate to managing analysis of electrocardiograms (ECGs) associated with a clinical trial. In some embodiments, ECGs can be processed by determining a technician to receive an ECG for measurement based on one or more factors and/or by determining a cardiologist to receive an ECG for measurement based on one or more factors. Examples of factors include a requested completion time associated with a clinical trial, the amount of distributed ECGs in each technician queue, and other protocol data associated with a clinical trial.

A modification to protocol data can be identified and the ECGs can be analyzed to determine which of the ECGs, if any, are to be reprocessed in accordance with the modified protocol data. Examples of modifications to protocol data include associating the ECGs to a different clinical trial, changing the requested completion time, and changing a protocol rule associated with the clinical trial. If one or more ECGs are determined to be reprocessed, a technician can be determined, based on one or more factors, to receive an ECG for measurement and/or a cardiologist can be determined, based on one or more factors, to receive a measured ECG for review.

These illustrative examples are given to introduce the reader to the general subject matter discussed here and are not intended to limit the scope of the disclosed concepts. The following sections describe various additional embodiments and examples with reference to the drawings in which like numerals indicate like elements, but the drawings and the accompanying description should not be used to limit the present invention.

Illustrative Data Flow for ECG Management

Figure 1:
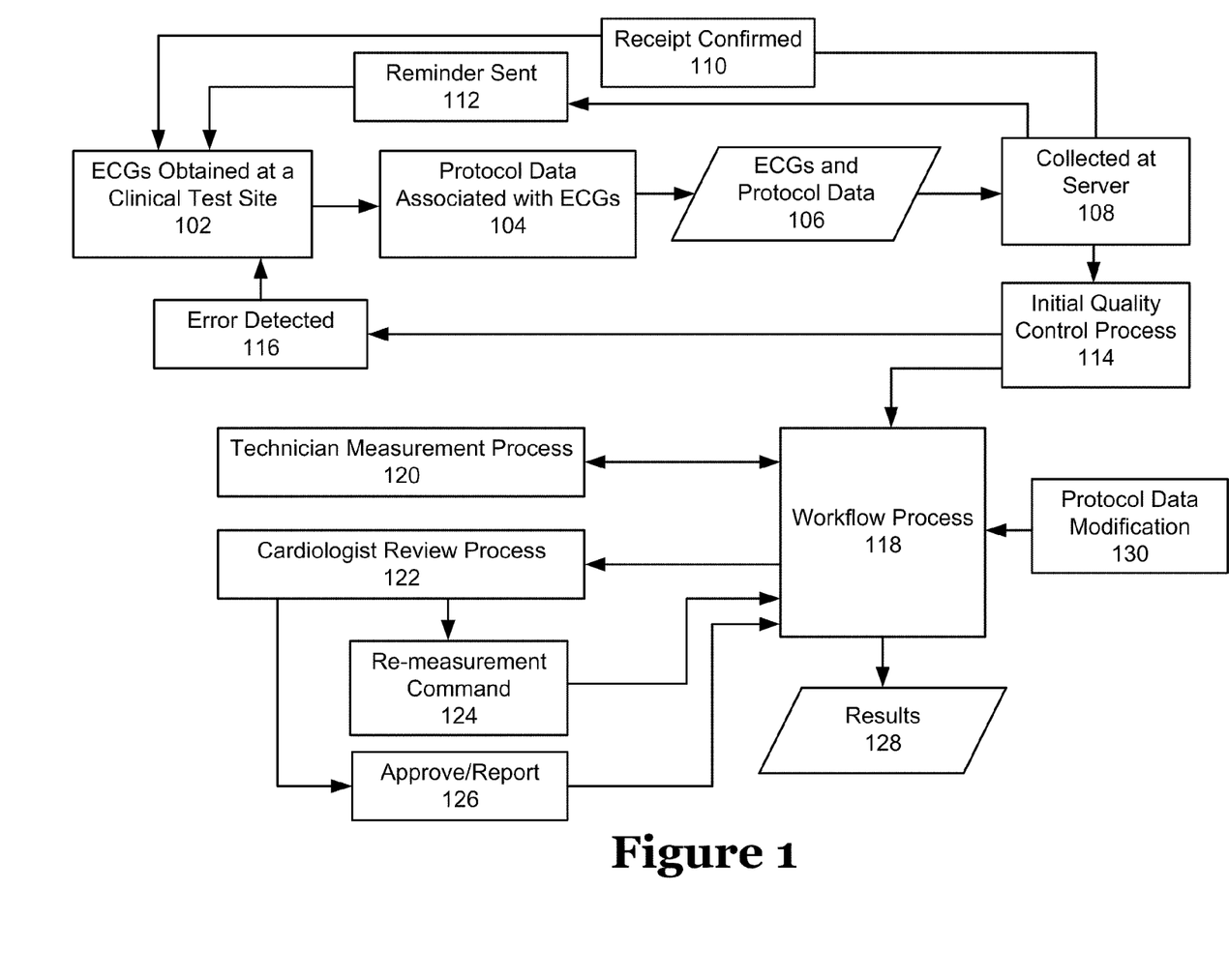
FIG. 1 is a data flow diagram of electrocardiogram (ECG) processing according to one embodiment of the present invention.

FIG. 1 shows a flow diagram of a data management process and procedure according to one embodiment of the present invention. According to the particular embodiment illustrated in FIG. 1, ECGs are obtained at a clinical test site 102. An ECG can be obtained by trained medical personnel such as a nurse, doctor, or clinical technician using leads attached to various points on a patient's body. An electrical measurement is read from each lead over time and this data is collected and placed in graph format showing voltage or other electrical parameters along with time relative to the starting time. Protocol data can be associated with each of the ECGs 104. The protocol data can include one or more rules by which the ECG is to be processed or otherwise managed and can also include an identification of the protocol to which the protocol data is associated. Other information, such as patient identifiers, clinical trial site identifies, and thresholds to set off an alarm, can be associated with the ECG.

ECGs and protocol data 106 can be provided by a device at the clinical trial site over a network and are collected at a server 108. The ECGs and protocol data can be provided in a digital format. The server, which may be located at any location, can be in communication with the network and can translate the ECGs and protocol data into a variety of formats for further data management. For example, data of an ECG can be changed into Extensible Markup Language (XML) format. XML format allows the creation of customized tags or metadata that enable the definition, transmission, validation, and interpretation of data between applications and between organizations. The server may provide a receipt confirmation 110 to the clinical test site to validate that server received the ECG.

If a particular patient's ECG and associated protocol data has not reached the server by a certain time, the server can send a reminder 112 to the clinical test site that indicates a particular patient's ECG has not been received by the server and that the particular ECG is overdue. The server may provide the reminder 112 when, for example, the patient has not appeared at the testing center by a scheduled date or an error in the system occurred and the server did not receive the ECG.

After collecting the ECGs, the server can provide the ECGs and any associated data, such as protocol data, to an initial quality control process 114. The initial quality control process 114 can conduct a review of the ECG, protocol data, and patient information to check that the data complies with the protocol rules and/or other desired parameters (e.g. clinical trial criteria and consistency of the patient data compared with previously received patient data). The initial quality control process 114 can include a human and/or a computer system performing aspects of the review relative to set criteria to check the data for inconsistencies with previously known patient data. If the initial quality control process 114 detects an error or an inconsistency, it can provide a notification of a detected error 116 to the clinical test site, which can seek to correct the error.

If the initial quality control process 114 does not indicate an error, the ECG and associated data can be provided to a workflow process 118. The workflow process 118 can include a workflow system, embodiments of which are described below, that is capable of managing the processing the ECGs. Processing an ECG can include managing the technician measurement process 120, managing the cardiologist review process 122, and routing ECGs in accordance with commands such as a re-measurement command 124, an approve/report command 126, and a protocol data modification 130. A protocol data modification can include a change to one or more rules associated with one or more ECGs. The workflow process 118 can identify the ECGs affected by the protocol data modification 130 and cause the identified ECGs to be reprocessing. The workflow process 118 can also output results 128, which may be measured ECGs and a report from a cardiologist for each ECG. The results 128 can be provided to data storage, a client, a regulatory agency, or any appropriate entity or organization.

Illustrative System Implementation for ECG Processing

Figure 2:
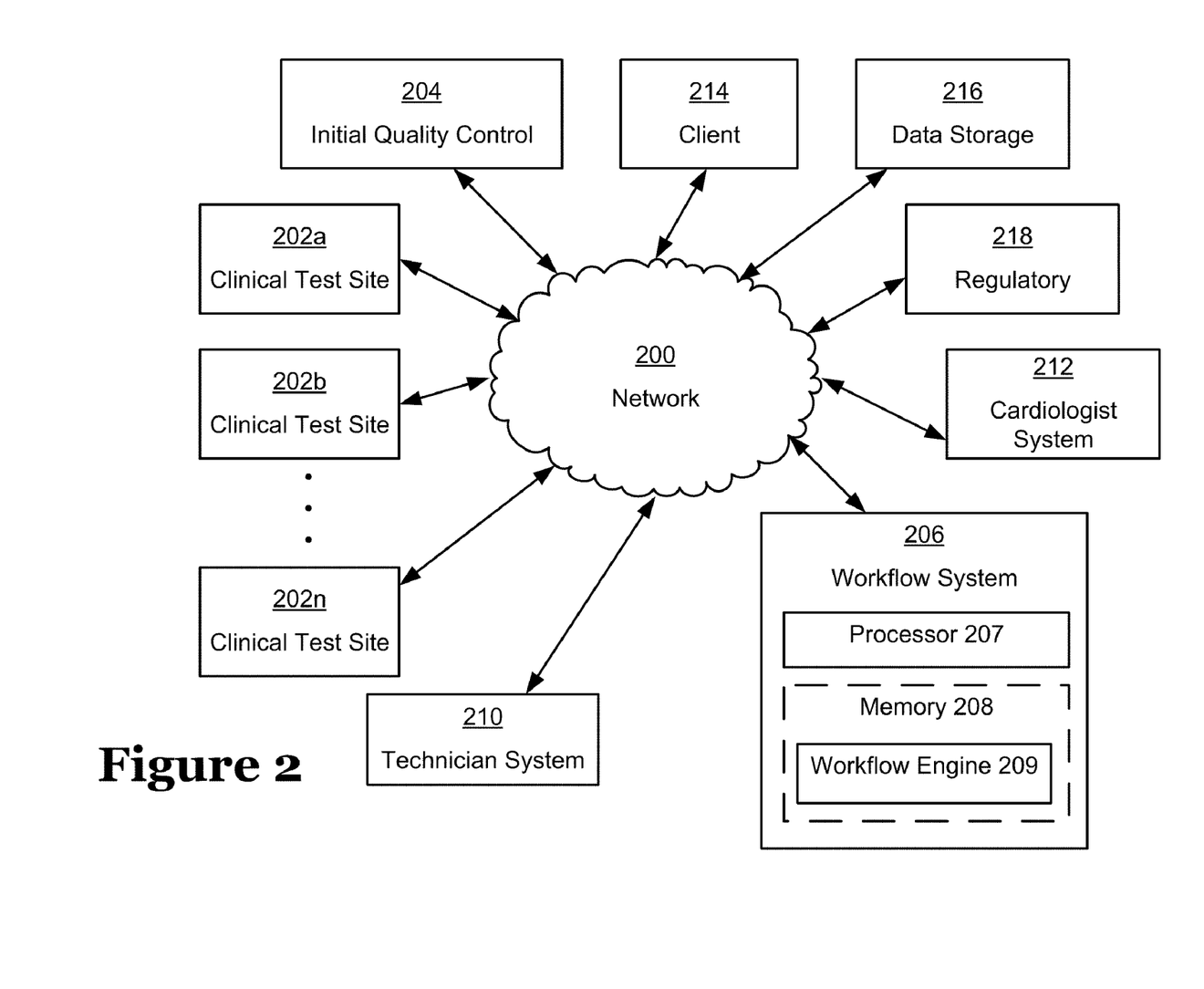
FIG. 2 depicts a workflow system according to one embodiment of the present invention that is capable of communicating with various systems and organizations through a network.

FIG. 2 depicts a network 200 through which various systems and organizations can communicate to allow for ECG data management. The Network 200 may be any system and include various components capable of allowing data to be communicated from one location to another location. Examples of network 200 include a computer network, Internet, a public switched telephone network, an intranet, wireless, and satellite communications network.

Clinical test sites 202a-n can be coupled to the network 200 to transmit and receive data. Transmitting data can include transferring the data over the network. The clinical test sites 202a-n can be organizations that perform ECG tests, obtain ECGs, obtain patient information, and provide the information, along with a destination address, to the network 200. The clinical test sites 202a-n can be located at various locations—even remote from each other—including anywhere in the world.

The network 200 can be configured to allow the clinical test sites 202a-n to communicate with other organizations and systems. For example, the network 200 can allow ECGs and associated data to be transmitted from the clinical test sites 202a-n to an initial quality control 204, which can be at any location and can be remote to each of the clinical test sites 202a-n. The initial quality control 204 can perform a cursory review, either automatically or by receiving inputs from a user (or both), of the associated data to ensure that all necessary information included with the associated data. The initial quality control 204 may confirm receipt with the clinical test site from which the data originated through the network 200. After the initial quality control 204 performs the cursory review and confirms accurate information, the ECGs and associated data can be transmitted through the network 200 to a workflow system 206.

In some embodiments, the workflow system 206 can provide a confirmation notification to the initial quality control 204 after successfully receiving the ECGs and associated data. The workflow system 206 includes a processor 207 that can execute code stored on a computer-readable medium, such as a memory 208, to cause the workflow system to managing workflow of ECG processing. Examples of the workflow system 206 include a desktop personal computer, a laptop personal computer, a server device, a handheld computing device, and a mobile device. The workflow system 206 may also include two or more devices located in the same or different location that are configured to perform various methods according to various embodiments of the present invention.

Examples of the processor 207 include a microprocessor, an application-specific integrated circuit (ASIC), a state machine, or other suitable processor. The processor 207 may include one processor or any number of processors. The processor 207 can access code stored in the memory 208 via a bus or otherwise. The memory 208 may be any tangible computer-readable medium capable of storing code. The memory 208 can include electronic, magnetic, or optical devices, capable of providing processor 207 with executable code. Examples of the memory 208 include random access memory (RAM), read-only memory (ROM), a floppy disk, compact disc, digital video device, magnetic disk, an ASIC, a configured processor, or other storage device capable of tangibly embodying code.

In some embodiments, the workflow system 206 is coupled to one or more other devices through which users or other systems can interact with the workflow system. Examples of such other devices include another computer or server, a keyboard, a mouse device, a touch screen interface, a display, and another network.

Instructions can be stored in the memory 208 as executable code. The instructions can include processor-specific instructions generated by a compiler and/or an interpreter from code written in any suitable computer-programming language, such as C, C++, C#, Visual Basic, Java, Python, Perl, JavaScript, and ActionScript. The instructions can include a workflow engine 209 that, when executed by the processor 207, can cause the workflow system 206 to manage ECG processing.

In some embodiments, the workflow system 206 receives ECGs, associated data, and information about a technician system 210 and information about a cardiologist system 212. The workflow system 206 can manage ECG processing using this data and information. For example, the workflow system 206 can use the data and information to determine which technician should receive an ECG for measurement to complete the measurements of the ECGs efficiently. In some embodiments, the workflow engine 209 can apply different weights to various factors and apply the factors to the data and information to determine which technician should receive an ECG for measurement. The workflow engine 209 can provide to the technician system 210 the ECG and identification of the technician to receive the ECG for measurement.

The workflow engine 209 can be configured to receive a measured ECG and a biometric signature from the technician system 210. The biometric signature can include electronic information concerning the time, date, personnel identification, or any other information related to the biometric signature of the technician that performed the ECG measurement. The biometric signature can be added to the data associated with the ECG to promote data security and integrity.

The workflow engine 209 can use the data and information to determine which cardiologist should receive a measured ECG for review to complete a report for the ECGs efficiently. The workflow engine 209 may use a similar process as for the technician to determine the cardiologist to receive the measured ECG. The workflow engine 209 can provide to the cardiologist system 212 the measured ECG and an identification of the cardiologist to receive the measured ECG for review. In some embodiments, the workflow engine 209 can receive a report for the ECG from the cardiologist system 212 that includes a biometric signature of the cardiologist.

In some embodiments, the workflow engine 209 can receive a modification to the data associated with the ECG. The modification may be a change to protocol data that specifies the clinical trial and specifies various rules by which the ECG is to be processed. For example, the protocol data may specify that a certain value to be obtained via a measurement. The workflow engine 209 can be configured to identify one or more ECGs from the group of ECGs that require reprocessing because of the modification and to cause the identified ECGs to be reprocessed to receive another report After receiving a report for the ECG —whether reprocessing was required or not—the workflow system 206 can provide the ECG, data associated with the ECG, and the report to one or more systems or organizations through the network 200. The destination of the report may depend on commands received from the cardiologist. For example, the report can include a command for a technician to re-measure the ECG at which the workflow engine 209 can re-distribute the ECG to a technician (the technician that originally measured the ECG or a new technician, depending on the command and/or the configuration of the workflow engine 209) for re-measurement.

The workflow system 206 can provide completed reports to systems or organizations such as a client 214, data storage 216, and a regulatory organization 218. The client 214 may be a protocol supervisory or other entity that is funding or managing the clinical trial. Data storage 216 may be a facility located at any location, for example Midwest United States, that stores the received information electronically and in a logical arrangement for later access. The regulatory organization 218 may be a government organization, such as the Federal Drug Administration (FDA) in Washington, D.C., that regulates clinical trials. The ECG and associated data may be reviewed, including biometric signature and other history data, by any group or entity with permission to view the record; alternatively, aspects of biometrics or confirmation that the data is protected by biometric signatures but in a manner that protects confidentiality or privacy, can be provided.

Figure 3:
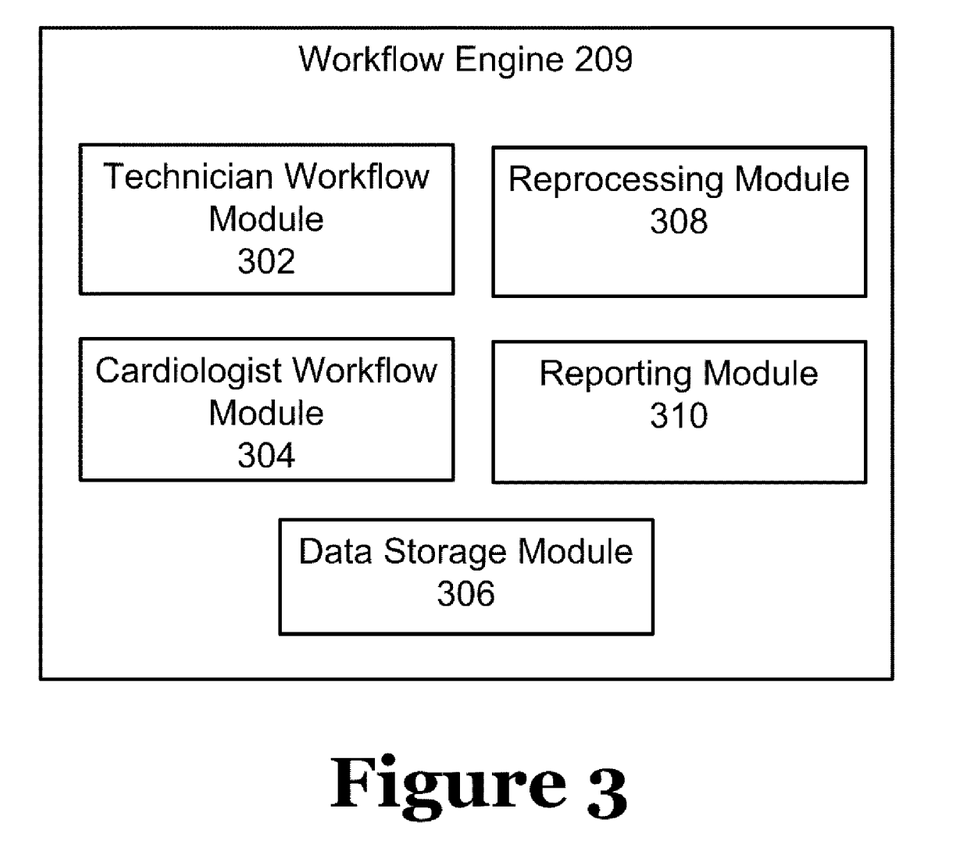
FIG. 3 is a block diagram of a workflow engine according to one embodiment of the present invention.

Workflow engines according to various embodiments of the present invention can include one or more modules capable of performing methods according to various embodiments of the present invention. FIG. 3 depicts the workflow engine 209 that includes five modules, but workflow engines according to embodiments of the present invention can include any number of modules. Each module may be a computer program or part of a computer program that, when executed by the processor 207, is configured to cause the workflow system 206 to perform actions. The modules shown in FIG. 3 include a technician workflow module 302, a cardiologist workflow module 304, a data storage module 306, a reprocessing module 308, and a reporting module 310.

The technician workflow module 302 is configured to cause the workflow system 206 to manage the technician workflow processes. The cardiologist workflow module 304 is configured to cause the workflow system 206 to manage the cardiologist workflow processes. The data storage module 306 is configured to cause the workflow system 206 to manage data storage, in the workflow system 206 and/or at an external data storage device. The reprocessing module 308 is configured to cause the workflow system 206 to analyze ECGs and data associated with the ECGs to determine whether to reprocess the ECGs after receiving a modification to protocol data. The reporting module 310 is configured to cause the workflow system 206 to format a report about an ECG or a group of ECGs and provide the report over the network 200.

Figure 4:
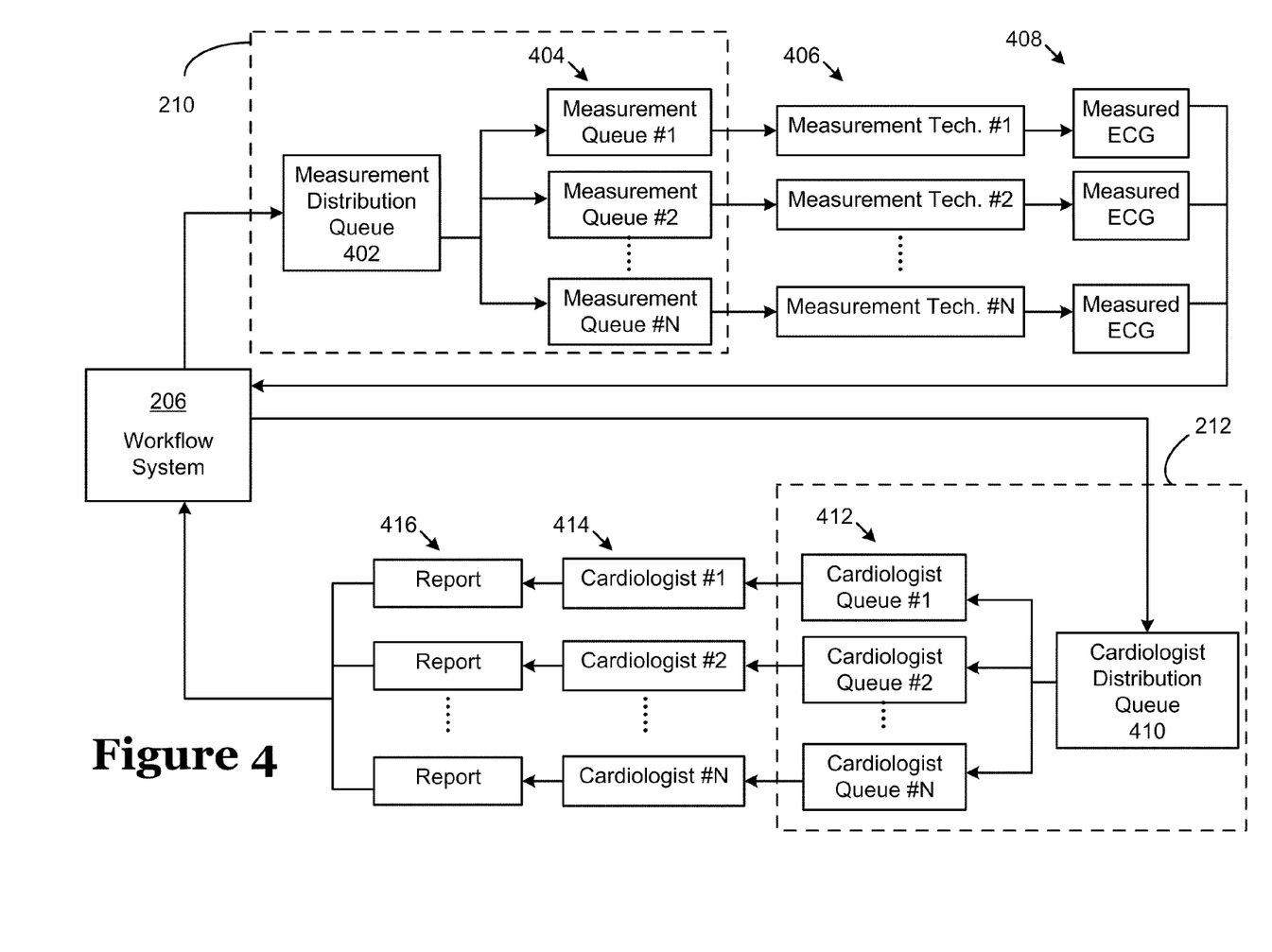
FIG. 4 is a block diagram of a workflow system in communication with a technician system and a cardiologist system according to one embodiment of the present invention.

FIG. 4 depicts the workflow system 206 communicating with the technician system 210 and the cardiologist system 212 according to one embodiment of the present invention. In some embodiments, the technician system 210 and the cardiologist system 212 are similar systems and receive and route information based on similar factors. The workflow system 206 provides ECG and associated data to the technician system 210 in a digital file with several addresses that may be associated with different types of data. The types of data could include, among others, the destination address of the data, the origination address, clinical protocol information, identification of personnel associated with the ECG, the ECG, and patient information. The file can be transmitted electronically to a measurement distribution queue 402 in the technician system 210.

The measurement distribution queue 402 can be a processor-based device that includes a processor, storage means, and inputs and outputs. The measurement distribution queue 402 may be in electrical communication with the measurement queues 404, each associated with a measurement technician from a group of technicians 406 on duty. The measurement queues 404 can be processor-based devices with a processor, inputs and outputs, and a storage means, and can include information such as the number of ECGs waiting to be measured, identification of each ECG, the amount of time left on the ECG before the analysis is to be completed, the abilities and efficiency of particular technicians, and the amount of time left on a technician's shift.

The workflow system 206 can configure the technician system 210 using information related to the ECGs and the technicians to cause the process of reviewing ECGs more efficient, effective and timely. For example, the workflow system 206 can cause the measurement distribution queue 402 to route received ECGs and associated information to a particular measurement technician among technicians 406 based on factors. The measurement distribution queue 402 can distribute an ECG to a measurement technician queue in accordance with the command from the workflow system 206.

Factors which may be utilized by the workflow system 206 to determine which technicians should receive a particular ECG for measurement can include any or all of the following, or any combinations of any of the following: (1) identification of the particular clinical trial, (2) amount of time left before the ECG measurement and analysis needs to be completed, (3) the category or nature of analysis or review that needs to be applied to the ECG, (4) the number of ECGs for a particular clinical trial that are already queued for routing to each technician, (4) the number of ECGs per category that are already queued for routing to each technician, (5) the number of ECGs in general that are queued for routing to each technician, (6) the number of technicians on duty at each location, (7) the number of technicians on duty that are qualified to review ECGs for a particular clinical trial or category, (8) the number of technicians on duty generally, (9) the time left on each technician's shift, (10) the cost per unit time for each technician as measured for a particular shift or other desired time interval, (11) specific circumstances for a clinical trial or ECG that preclude sending the ECG data to particular technicians, or technicians in a certain country or location, (12) specific circumstances for a trial or ECG that preclude or favor sending the ECGs to a particular technician or group of technicians, (13) the rejection rate of ECGs performed by each technician, or (14) any other factors as may be desired related to efficiently managing workflow to produce results with adequate quality.

For example, if the measurement queue #1 associated with measurement technician #1 includes a high number of different ECGs waiting to be measured by the technician and measurement queue #2, associated with measurement technician #2, includes a low number of different ECGs waiting to be measured, the workflow system 206 can command the measurement distribution queue 402 to distribute new ECGs to measurement queue #2 for measurement. Additionally, the workflow system 206 can be configured to monitor the amount of ECGs in each measurement queue 404 and may cause the measurement distribution queue 402 to remove ECGs from the measurement queue #1 and distribute it to measurement queue #2. In determining the measurement queue to which to distribute new ECGs or to re-distribute distributed ECGs, the workflow system 206 can identify, for example, the ECGs in the respective measurement queues 404 and determine the amount of time left for each ECG before the analysis is scheduled to be complete. Furthermore, the workflow system 206 can receive information associated with the respective measurement technicians 406, such as the amount of time left on each technician's shift, and use the information to determine the number of ECGs to distribute to each queue to ensure ECGs in a technician's queue are measured before the shift for that technician ends.

In some embodiments, the workflow system 206 determines credentials associated with each technician and determines the technician to receive an ECG for measured based on the credentials and the protocol data associated with the ECG. Credentials can include any quantitative or qualitative measurement of a technician's experience and ability in measuring or otherwise processing ECGs. Some credentials can indicate a technician's ability to perform certain types of measurements. The workflow system 206 can determine the technicians that have credentials matching those specified by the protocol data.

After the measurement technicians 406 perform measurements, such as by using a processor-based device to review and annotate ECGs, measured ECGs 408 can be outputted to the workflow system 206. The measured ECGs 408 can include the ECG and measurement data that represents the values of the measurements performed by the measurement technicians 406. In some embodiments, the workflow system 206 can require each measurement technician to provide a biometric signature that is an electronic representation of a fingerprint or other unique feature of the technician and that is associated with the ECG and measurements. A device may be provided that receives the fingerprint and compares it to a database containing the fingerprints various measurement technicians, an identification associated with the fingerprint, and information concerning what the measurement technician may electronically save or transmit. Once the measurement technician has successfully provided a biometric signature, information such as the time, date, and identification of the particular measurement technician can be electronically attached to the particular ECG. Attaching the biometric signature may, for example, provide an audit trail to provide interested and allowed parties to recreate the path by which a particular ECG traversed. Selectively disclosing data provides data verification quality control while protecting any privacy interests associated with the data or the collection, management, and analysis personnel.

The workflow system 206 can provide the measured ECGs (and other associated data) to a cardiologist distribution queue 410 of the cardiologist system 212. The cardiologist distribution queue 410 may be similar to the measurement distribution queue 402. The cardiologist distribution queue 410 can be in electrical communication with cardiologist queues 412, each of which is associated with one of the on-duty cardiologists 414. The workflow system 206 can receive information about the cardiologist queues 412 from the cardiologist distribution queue 410 and provide commands to the cardiologist distribution queue 410 to command measured ECGs for analysis to certain queues among the cardiologist queues 412 based on one or more factors.

Factors can include any or all of the following: (1) identification of the particular clinical trial, (2) amount of time left before the ECG measurement and analysis needs to be completed, (3) the category or nature of analysis or review that needs to be given to the ECG, (4) for each cardiologist, the number of ECGs for a particular clinical trial that are already queued, (4) for each cardiologist, the number of ECGs per category that are already queued, (5) for each cardiologist, the number of ECGs in general that are queued, (6) the number of cardiologists on duty at each location, (7) the cardiologists on duty that are qualified to review ECGs for a particular clinical trial or category, (8) the number of cardiologists on duty generally, (9) the time left on each cardiologist's shift, (10) the cost per unit time for each cardiologist as measured for a particular shift or other desired time interval, (11) any circumstances for a trial or ECG that preclude sending an ECG to a particular cardiologist, or cardiologists, in a certain country or location, (12) any circumstances for a trial or ECG that preclude or favor sending the ECGs to a particular cardiologist or group of them, (13) the rejection rate of ECGs reviewed by each cardiologist, and/or (14) any other factors as may be desired related to efficiently managing workflow to produce results with adequate quality.

If the cardiologist queue #1 associated with cardiologist #1 has a high number of measured ECGs and/or there is a low amount of time left in cardiologist #1's shift, embodiments of the workflow system 206 can cause measured ECGs to be distributed to a different cardiologist queue, such as another cardiologist queue #2, that has a lower number of measured ECGs and/or there is a higher amount of time left on cardiologist #2's shift. In addition, the workflow system 206 can cause the cardiologist distribution queue 410 to remove measured ECGs from the queues after monitoring the queues using one or more factors.

After the cardiologists 414 review measured ECGs, reports 416 can be created. A report can specify that the cardiologist affirms the measurement by the technician, include a command for the ECG to be re-measured, include recommendations for patient follow-up, or other information about the cardiologist's conclusion after reviewing the measured ECG data. In some embodiments, the report can include a biometric signature of the cardiologist that reviewed the measured ECG.

If the report includes a command for re-measurement, the workflow system 206 can cause the ECG to be reprocessed by provided it to the technician system with a command for distribution. The command may be to have the original technician conduct the re-measurement, or to have a different technician conduct the re-measurement. The measurement distribution queue 402 can be responsive to the command to distribute the measured ECG to a measurement queue.

If the ECG does not need to be reprocessed, the report and the ECG can be transmitted by the workflow system 206 to another organization or system, such as a client 214, data storage 216, or regulatory 218, as depicted in FIG. 2.

In some embodiments, the workflow system 206 can receive a modification to protocol data after an ECG or group of ECGs have been processed by being measured and having the measurements reviewed by the cardiologists 414. The workflow system 206 can analyze the ECGs in view of the modification to identify which, if any, ECGs need to be reprocessed in accordance with the modification to the protocol data. The workflow system 206 can cause the identified ECGs to be reprocessed by providing the identified ECGs to the technician system 210 and/or the cardiologist system 212. For example, the modification may indicate that certain ECGs need to be re-reviewed, but not re-measured. Other modification may indicate that certain ECGs need to be re-measured and re-reviewed.

Illustrative Methods for Managing ECG Processing

Figure 5:
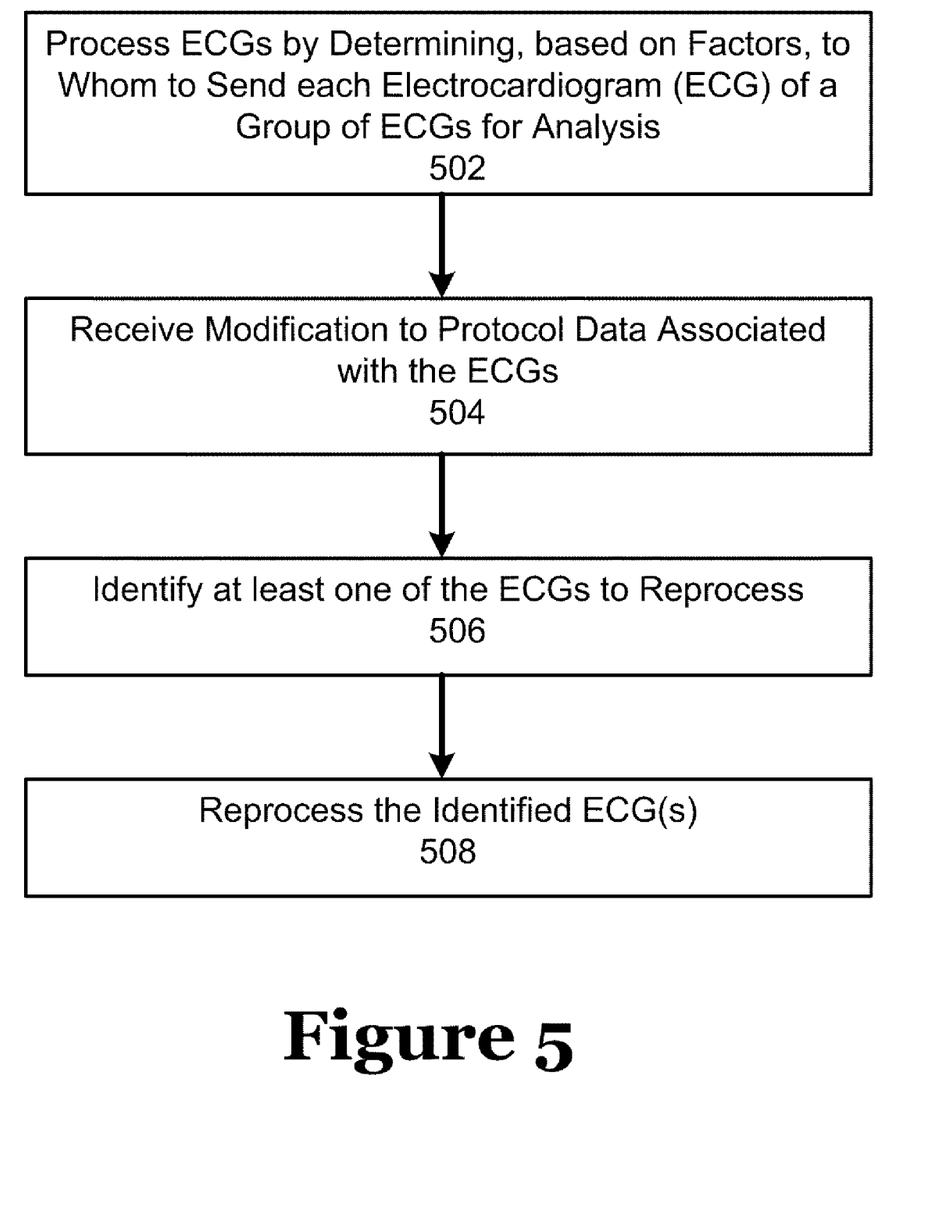
FIG. 5 is a flow diagram of a method for managing ECG(s) according to one embodiment of the present invention.

Various methods according to various embodiments of the present invention can be used to manage ECG processing. FIG. 5 is a flow chart of method for managing ECG processing according to one embodiment of the present invention.

Figure 6:
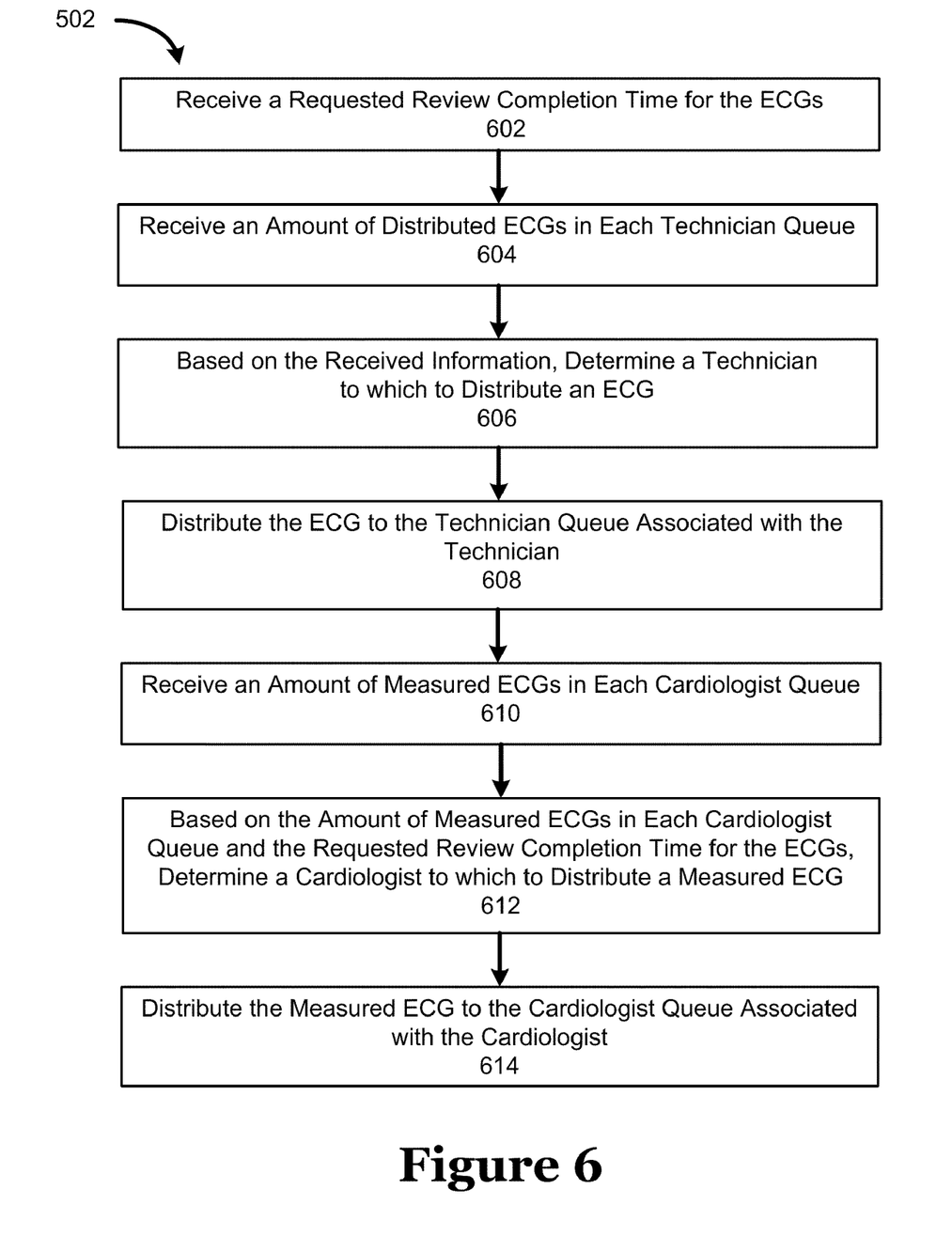
FIG. 6 is a flow diagram of a method for processing ECG(s) according to one embodiment of the present invention.

In block 502, a workflow engine processes ECGs by determining the technician to receive an ECG and/or the cardiologist to receive a measured ECG, based on factors. The factors can include any information about the queues of the technicians, the queues of the cardiologists, the technicians, the cardiologists, the protocol data, the ECG, or otherwise about anything associated with ECG processing. FIG. 6 depicts one embodiment of a method for processing ECGs based on factors that include an amount of distributed ECGs in each technician queue and the requested review completion time for the ECGs.

In block 602, the workflow engine receives the requested review completion time for the ECGs. The requested review completion time may be a deadline associated with an ECG or a group of ECGs by which the cardiologist review needs to be completed. An example of a requested review completion time is 24 hours from the time that the ECG was transmitted from the clinical test site.

In block 604, the workflow engine receives an amount of distributed ECGs in each technician queue. Each technician may be associated with one technician queue. The technician queue can include ECGs waiting to be measured by the technician. By receiving the amount of distributed ECGs in a technician queue, the workflow engine can determine the workloads associated with each technician. The workflow engine may also receive a shift ending time for each technician or other information about the technician, technician queue, or otherwise. For example, the workflow engine can receive an efficiency rating for each technician and use the efficiency rating, which may represent the efficiency of the technician, to make ECG distribution decisions.

In block 606, the workflow engine determines a technician to which to distribute an ECG based on the amount of distributed ECGs in each technician queue and the requested review completion time. For example, if the requested review completion time is near, the workflow engine can identify the technician that has a lowest number of distributed in his or her queue to review. If the requested review completion time is far from the current time, the workflow engine can identify a technician that has a medium or high number of ECGs in his or her queue to which to distribute the ECG to reserve technicians with low amounts of ECGs in queues for more time sensitive ECGs. This process can be repeated for each ECG and can be based on different or additional information about the ECG, the technicians, the technician queues, or otherwise.

In block 608, the workflow engine can cause the ECG to be distributed to the technician queue associated with the technician determined to receive the ECG for measurement. The technician can use a measurement device—which may be measurement software executing on a processor-based device—to measure the ECG and cause a measured ECG to be returned to the workflow engine for distribution to a cardiologist for review. In some embodiments, the workflow engine provides measured ECGs to a cardiologist system for review without providing distribution decisions to cardiologist queues or otherwise. In other embodiments, the workflow engine can determine a cardiologist to which to distribute an ECG, as explained below.

In block 610, the workflow engine receives an amount of measured ECGs in each cardiologist queue. The workflow engine may also receive other information, such as the time left on a shift for each cardiologist—similar to the technician queue information.

In block 612, the workflow engine can determine a cardiologist to distribute a measured ECG based on the amount of measured ECGS in each cardiologist queue and the requested review completion time associated with the measured ECG. The cardiologist determination can be similar to the technician determination. The determination can allow measured ECGs to be reviewed more efficiently and can allow measured ECGs that are time sensitive to be timely reviewed.

In block 614, the workflow engine distributes the measured ECG to the cardiologist queue associated with the cardiologist determined to receive the measured ECG for review. The cardiologist can use software executed by a processor-based device to review the measurements of the ECG to confirm the measurements, identify the ECG for re-measurement, and/or identify a medical issue to be flagged for the patient based on an analysis of the ECG. For example, the cardiologist can generate a report that includes the review results. The report can be returned to the workflow engine. The workflow engine can provide the ECG and associated report to one or more systems or organizations, including data storage.

Returning to FIG. 5, the workflow engine receives a modification to protocol data associated with the ECGs in block 504. Protocol data can be rules by which the ECGs are processed. Examples of protocol data include the particular measurements to be obtained and reviewed, the clinical trial with which the ECGs are associated, credentials required of a technician or cardiologist to process the ECGs, etc. A modification to the protocol data can include any change to the protocol data that triggers a need to determine whether one or more ECGs need to be reprocessed because the processing results are not in accordance with the modification. Examples of modification to protocol data include changing the clinical trial with which the ECGs are associated and changing a measurement that is needed for the ECGs.

In block 506, the workflow engine identifies the ECGs that need to be reprocessed because of the modification to the protocol data. In some embodiments, the workflow engine compares the processing results for each ECG to the modified protocol data to determine whether the processing results meets the requirements in the modified protocol data. If the processing results for certain ECGs do not meet the requirements, the workflow engine can identify them for reprocess.

In block 508, the workflow engine causes the identified ECGs to be reprocessed. For example, the workflow engine can distribute the ECGs to the technician system and/or the cardiologist system, for example as described with reference to FIG. 6, for re-measurement and/or re-review.

ILLUSTRATIVE EXAMPLES

Figure 7:
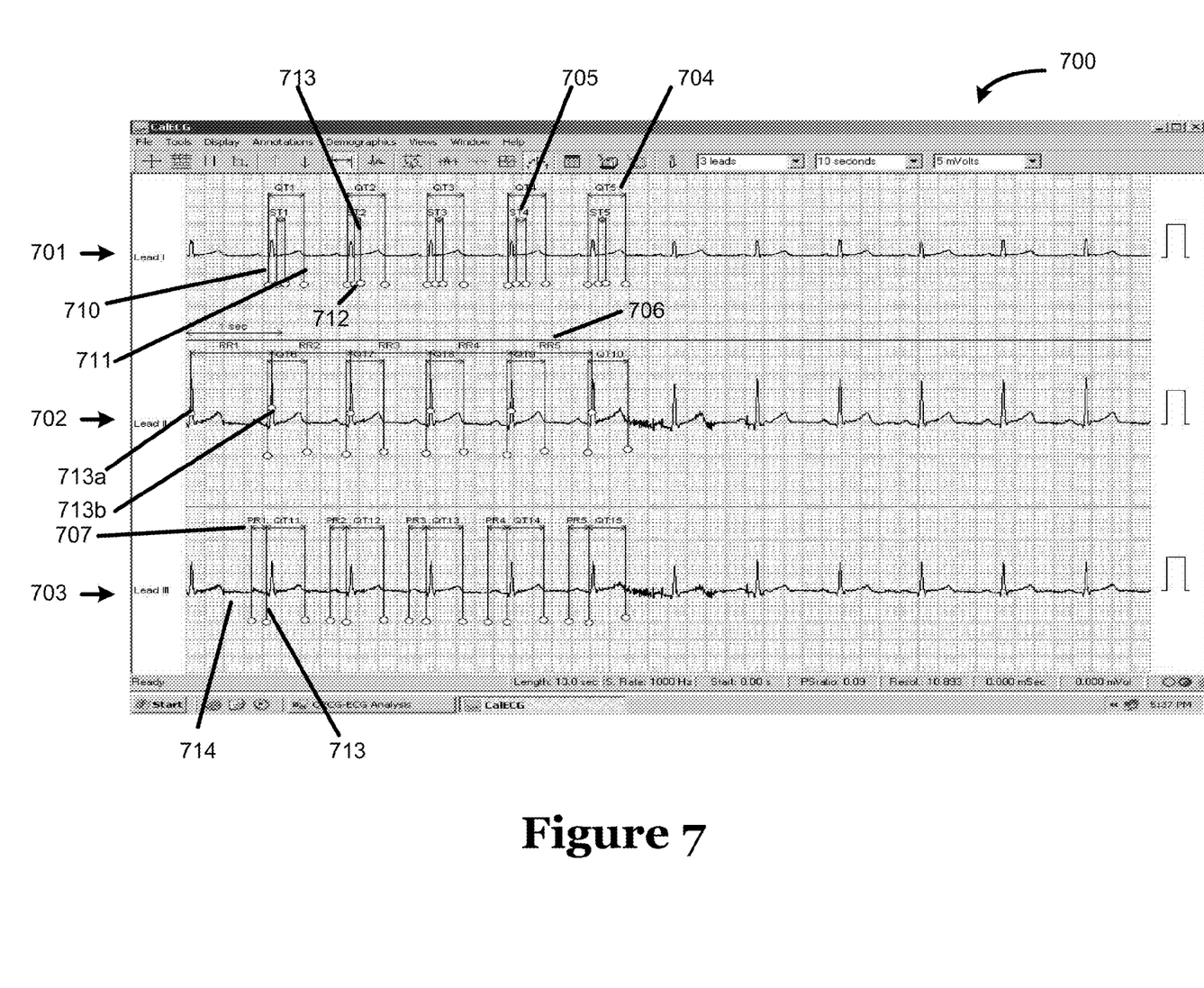
FIG. 7 depicts an example of graphed ECG data and measurements according to one embodiment of the present invention.

FIG. 7 depicts a sample ECG that is graphed with measurements according to one embodiment of the present invention. The ECG 700 includes data from three leads 701, 702, 703 and it is shown as a function of voltage with respect time. Although the specific traces shown in FIG. 7 illustrate data from only three leads 701, 702, 703, an ECG can include from any number of leads.

In FIG. 7, measurements for the QT 704, ST 705, RR 706 and PR 707 values are shown. A measurement technician has applied electronic calipers to the ECG 700 and labels, such as QT, ST, RR, and PR. As illustrated, the QT 704 value is measured on all three leads and is measured from the start of the Q wave 710 to the end of the T wave 711. The QT 704 may be obtained from any number of leads, including one lead. The ST 705 can be measured from at least one lead of the ECG 700 and is the distance between the QRS complex wave 713 and the T wave 712. The RR 706 value can be measured from the beginning of one QRS complex wave 713a to the beginning of the next QRS complex wave 713b. The RR 706 value can be measured from at least one lead of the ECG 700. The PR 707 value can be measured from at least one lead and is measured from the P wave 714 to the QRS complex wave 713.

Each of the above measurements can be performed multiple times on one or more leads of the ECG 700. After accumulating the measurements for each value, a data table can be populated with the values, such as average values for each type of measurement. Alternatively, the data table can be populated with a value for each measurement for each data type or with any other data based on the cumulative data. In other embodiments of the present invention, the measurement technician can manually enter the data associated with the measurements into tables. The tables can be associated with the ECG and can be accessible for future review by a reviewing cardiologist, clinical trial supervisor, testing center personnel, the FDA, or any other entity with permission to view the measurements.

In some embodiments of the present invention, a terminal is provided that is in electrical communication with, for example, the servers, initial quality control, measurement workflow system, cardiologist workflow system, and the post-analysis diagnosis system. The terminal preferably provides the ability to track where each ECG data file is located in the system at any particular time and to determine the status of such ECG data, as well as allowing other observation, monitoring and control over flow of data and work in the system.

Figure 8:
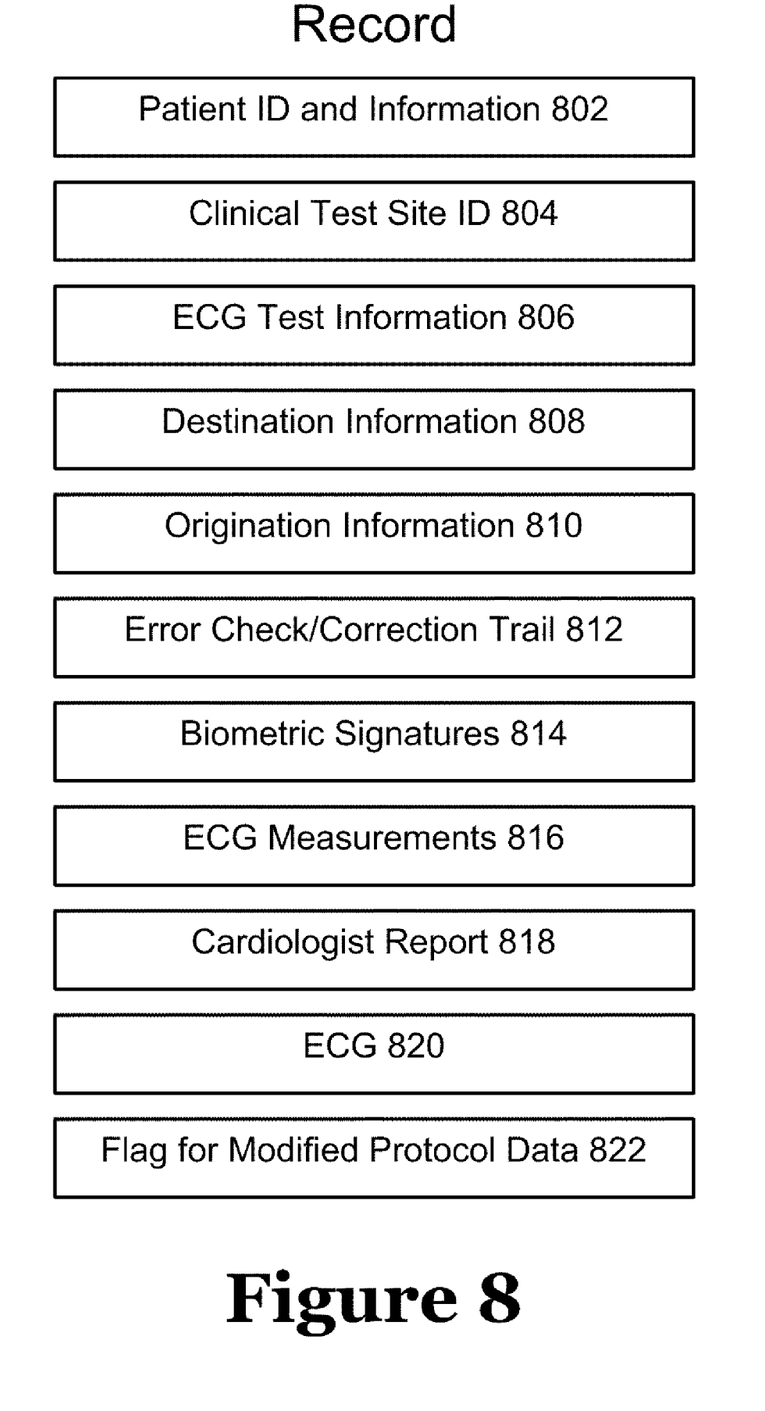
FIG. 8 is a record file of an ECG and associated data according to one embodiment of the present invention.

FIG. 8 depicts data elements of an ECG record according to one embodiment of the present invention. Data records can include information related to the ECG and the ECG itself. The data records may be electronic and transferable between various organizations and systems. The data record shown in FIG. 8 includes a number of different types of data 802-822. For example, the record may include patient identification and information 802 such as a name or number that may be associated with a name, gender, age, race, or any other patient information pertinent to a clinical trial. Another data record can include a clinical test site identification 804, such as the testing center location, personnel identification, or any other information related to the test site and that may identify the site.

The record may also include ECG test information 806, such as the test protocol, drug or medical procedure being tested, or information related to the test protocol. The ECG test information 806 can also include normal or acceptable data parameters, such as normal ECG measurement ranges or any other type of information related to the test protocol.

The record can include destination information 808 and origination information 810. Destination information 808 and origination information 810 may include, for example, the location, time, and date of the organization or system that is the origination or destination of ECG information and the record at each transfer instance in the system.

In addition, the record can include error check/correction trail 812 to provide a digital check on the ECG data and insure the integrity and accuracy of the digital ECG data. Furthermore, the record can include biometric signatures 814, such as the time and date of the biometric signature and identification of a particular technician or cardiologist that performed measurements or analyzed the data, may be included in the record.

The record can also include ECG measurements 816 and a cardiologist report 520 from the technician system and the cardiologist system, respectively. For example, ECG measurements 816 can include the results from the technician's measurement of the ECG and the cardiologist report 818 can include the results from the cardiologist's review of the data. The cardiologist report 818 can also include comments regarding the ECG, recommendations as to diagnosis or treatment, and recommendations on whether the patient should continue participating in the protocol. The record includes the ECG 820, which may be in a digital form. The ECG 820 includes digital version of the values of the electrical signals with respect to time, as obtained at the test site.

The record can also include a flag for modified protocol data 822. The flag can be configured to indicate that protocol data, which may included in the ECG test information 806 or otherwise, has been modified. The flag for modified protocol data 822 can also include an identification of the protocol data that was modified. Workflow systems according to various embodiments of the present invention can detect the flag and cause the ECG to be analyzed to determine whether reprocessing is needed in view of the modified protocol data 822.

The following describes a specific predictive example of data management according to a specific embodiment of the present invention. A clinical trial is first planned and a protocol developed. The protocol includes the testing site information, visit schedule information, and the ECG criteria. The data management company enters the criteria electronically into their processing systems, quality check systems, and post-analysis diagnosis systems to compare to the ECG data, measurements, and analysis.

Patients agreeing to participate in the clinical trial visit testing centers to receive medication according to the trial, submit to an examination, and otherwise provide information based on the examinations and testing such as ECG data. Personal information is entered into a database located at the testing center. An identification number is associated with the patient's name and replaces the name to ensure patient privacy. Information from testing, such as ECG data, is converted to a digital format, and associated with the patient's information by creating an electronic record with several fields and entering the digital ECG data and patient information into the fields.

The record containing ECG data and patient information is then transmitted through a conventional telecommunications or data network to a network server. The network server uses E-Scribe provided by Mortara located in Milwaukee, Wis. or GE Marquette MUSE receiving software and hardware provided by GE Medical Systems located in Milwaukee, Wis. to convert the ECG data to the XML format. The network server also sends a full hand shaking data packet back to the transmitting ECG device to inform the testing center that the data was received. The network server then forwards data to an initial quality control. Upon receipt, the initial quality control informs the network server indicating that the data was received.

The initial quality control includes a computer system connected to the network that receives the data and displays the patient information and ECG data on a screen for an initial quality control technician to review the data for inconsistencies. If previous patient information is present on a database accessible by the initial quality control computer, that information can displayed side-by-side with the new patient information on the computer screen. The initial quality control reviews the sets of information for inconsistencies and for incorrect information, such as a patient age of 130 years. If the initial quality control review indicates inconsistent or incorrect data, a data correction form is transmitted to the original testing center seeking verification or correction of the data. If no inconsistent or incorrect data are detected, or if the data is verified or corrected by the original testing center, the initial quality control sends the data record electronically to a measurement workflow system. Such error correction and/or messaging can also be conducted automatically using rules or partially automatically with the aid of a reviewer.

Before the information is electronically transmitted to the measurement workflow system, the initial quality control can require a biometric signature. The biometric signature is performed through the U-Match Matchbook version 3.0 hardware, utilizing Athenteon Software Appliances version 1.0 (BSDK 4.7 and 5.0), all provided by BioLink Technologies International, Inc. located in Coral Springs, Fla., which is connected to a database that contains biometric information associated with the technicians. If the technician submitting the biometric data is authenticated, validated, or permissioned by information in the database, the technician may be authorized to transmit the record. Once the biometric signature is determined to be valid, the identification of the personnel, time, and data of the signature can be automatically entered into the record with the ECG data. If the technician is not identified, the biometric signature system does not allow the technician to transmit the data.

The measurement workflow system receives the electronic data record of the ECG data, along with electronic data associated with the measurement technicians on duty. Such data associated with the technicians includes the number of technicians on duty, the time for each technician remaining on shift, the number of ECG data records waiting to be measured by each technician. The workflow system manages the volume of ECG data to be measured by allocating the data to the technician who is in best position to process it according to these criteria and this determination.

Once the workflow system determines to which technician to send the ECG data for measurements, the workflow system sends the particular record to that technician's queue. The technician queue stores the information while waiting for the technician to measure the ECG data already waiting in the technician queue. The technician queue can also notify the technician when the allocated time for a particular ECG data record to be measured is near expiration. The technician queue notifies the technician by listing each ECG data set waiting to be measured and highlighting the records in red with only an hour left on the allocated time, in yellow with between 1 and 2 hours left, and in green with more than 2 hours left. The technician is able to view the technician queue screen and select the particular ECG data with the least amount of time left in the technician's particular queue.

After selecting the particular ECG data, the technician utilizes CalECG version 2.0 software provided by A.M.P.S. located in Montichiari, Italy to obtain the ECG data in the form of a graph of the voltage with respect to time of three leads. The technician then uses the CalECG electronic caliper software provided by A.M.P.S. located in Montichiari, Italy to measure the desired values of QT, ST, RR, and PR on the graphed ECG data on a computer screen by locating the calipers with a mouse on the appropriate points on the graphed ECG data. When these values are measured, the value associated with these measurements automatically populates an electronic table and are entered into the ECG data record upon the technician saving the measurements.

Similar to the initial quality control, before the technician saves the data, the technician must submit a biometric signature by using the U-Match Matchbook version 3.0 hardware, utilizing the Athenteon Software Appliances version 1.0 (BSDK 4.7 and 5.0), provided by BioLink Technologies International, Inc. located in Coral Springs, Fla. If the technician has permission to save, the measurement data will be included into a field of the ECG record and electronic sent to a cardiologist workflow system.

The cardiologist workflow system is able to receive the information related to the amount of time left before the ECG data measurement and analysis must be completed, along with electronic information related to the particular cardiologists on duty. Such information includes the number of cardiologists on duty, the number of ECG data records waiting to be analyzed by each cardiologist, the cost per unit of time for each cardiologist, the cardiologist's historical efficiency and accuracy, and other relevant information including amount of time left before the ECG data analysis is due to be completed. The cardiologist workflow system will, based on the information related to the ECG data and cardiologists send the ECG data for review to the cardiologist that will most efficiently complete the analysis of the data. For instance, if the time left for the ECG data to be completed is 6 hours, the workflow system will determine which cardiologist would be most efficient at measuring the data while calculating, also, the possibility that ECG data that is later received by the workflow system may have only an hour left before it is to be completed.

Once the workflow system determines which cardiologist should receive the ECG data for analysis, the workflow system will electronically assign the ECG data to the particular cardiologist's queue. The cardiologist queue stores the ECG data and displays the presence and status of the data to the cardiologist while the cardiologist is measuring other ECG data. The technician queue will highlight the ECG data waiting to be analyzed in red if the time left until completion of that particular ECG data is less than 1 hour. If the time left is between 1 and 2 hours, the ECG data will be highlighted in yellow, while ECG data with time left of more than 2 hours will be highlighted in green.

The cardiologist uses the system to access the ECG data by clicking on the particular data to be measured. The system accesses the ECG data, patient information, and technician measurement data and displays the information on a screen viewable by the cardiologist. The cardiologist reviews the data and provides comments regarding whether the ECG data is (1) correctly measured by the technician, (2) if correctly measured, whether the ECG data is normal, (3) if abnormal, the recommended treatment, diagnosis or changes within the protocol should be made. The cardiologist also performs other analysis and supplies information and conclusions in a report, which may form part of the data.

Once the cardiologist completes the report, it can be saved the data after providing a biometric signature that is the same as or similar to the one previously described. The biometric signature data, when completed and successful, along with the cardiologist's report, will be entered into fields of the particular ECG data record and saved. If the measurements are incorrect, the cardiologist sends the data electronically to the measurement workflow system for re-measurement. The measurement workflow system will electronically read the audit trail associated with the ECG data and send the ECG data for re-measurement to the same technician who originally measured the data to provide feedback to the measurement technicians. If the measurements are correct, however, the report is transmitted electronically to a post-diagnosis analysis system.

The post-diagnosis analysis system is a computer system that can access a database with set protocol criteria relating to ECGs. The post-diagnosis analysis system receives the ECG data record and electronically compares the measured ECG values with the protocol ECG criteria to make sure that the ECG values are within the ECG criteria and thus provides an additional quality and safety check on the clinical test. If the ECG values are outside the set criteria, the post-analysis diagnosis system will deliver a message indicating values outside the set range to the original testing center and clinical trial supervisors.

A workflow system can receive a modification to protocol data. Examples of modifications to protocol data include a command to associate the ECGs with a different clinical trial and a change to one or more rules (such as measurement types) by which the ECGs are to be processed. The workflow system can identify the ECGs that require reprocessing because of the modification and can cause the identified ECGs to be reprocessed.

After the data have been prepared and verified by the system, one or more reports can be generated regarding the ECGs and accompanying trial information for transmission electronically and as otherwise desired to the original testing center, clinical trial supervisors, data storage facility, and the FDA.

The foregoing description of the embodiments, including illustrated embodiments, of the invention has been presented only for the purpose of illustration and description and is not intended to be exhaustive or to limit the invention to the precise forms disclosed. Numerous modifications, adaptations, and uses thereof will be apparent to those skilled in the art without departing from the scope of this invention.

What is claimed is:

1. A system comprising:
a processor; and
a computer-readable medium comprising code capable of being executed by the processor to:
receive a plurality of electrocardiograms (ECGs), each ECG being associated with protocol data, the protocol data comprising a requested review completion time and protocol rules;
receive a representation of an amount of distributed ECGs present in each technician queue among a plurality of technician queues;
receive a representation of an amount of distributed ECGs present in each cardiologist queue among a plurality of cardiologist queues;
process the plurality of ECGs to receive measurements of the plurality of ECGs and to receive results of cardiologists reviewing the measurements by:
determining a technician among the plurality of technicians to receive an ECG of the plurality of ECGs based on the requested review completion time for a clinical trial with which the ECG is associated and based on the representation of the amount of distributed ECGs present in each technician queue of a plurality of technician queues; and
determining a cardiologist among a plurality of cardiologists to receive for review an ECG of the plurality of ECGs and to receive a measurement associated with the ECG of the plurality of ECGs, based on the requested review completion time and based on the representation of the amount of distributed ECGs present in each cardiologist queue, to allow receipt of a report for the ECG from the cardiologist before the requested review completion time;
receive a modification to the protocol data;
identify, based on the modification to the protocol data, at least one ECG from the plurality of ECGs to be reprocessed; and
reprocessing, in accordance with the modification to the protocol data, the at least one ECG identified from the plurality of ECGs.

2. The system of claim 1, wherein the code is capable of being executed by the processor to transmit the report over a network.

3. The system of claim 1, wherein the modification to the protocol data comprises at least one of:
changing the protocol data for the clinical trial to the protocol data for a second clinical trial; or
changing at least one of: the requested completion time or a rule of the protocol rules.

4. The system of claim 1, further comprising:
an initial quality control system configured to:
perform an error check on the protocol data associated with the ECG; and
perform an error check on the ECG.

5. The system of claim 1, wherein the code capable of being executed by the processor to determine the technician among the plurality of technicians to receive an ECG, comprises determining the technician based on shift ending times for the plurality of technicians.

6. The system of claim 1, wherein the code capable of being executed by the processor to determine the ECG is to be reprocessed by determining the modification to the protocol data requires a specified measurement not present in the measurement of the ECG.

7. A method comprising:
receiving protocol data for a clinical trial, the protocol data comprising a requested review completion time and protocol rules;
receiving a plurality of electrocardiograms (ECGs) associated with the clinical trial, each ECG being associated with protocol data;
receiving a representation of an amount of distributed ECGs present in each technician queue among a plurality of technician queues;
receiving a representation of an amount of distributed ECGs present in each cardiologist queue among a plurality of cardiologist queues;
processing, by a device, the plurality of ECGs to receive measurements of the plurality of ECGs and to receive results of cardiologists reviewing the measurements, the device comprising a processor executing code stored on a computer-readable medium to cause the device to process the plurality of ECGs, the processing comprising:
based on a requested review completion time for the clinical trial and based on the representation of the amount of distributed ECGs present in each technician queue, determining a technician among a plurality of technicians to receive an ECG of the plurality of ECGs; and
based on the requested review completion time for the clinical trial and based on the representation of the amount of distributed ECGs present in each cardiologist queue, determining a cardiologist among a plurality of cardiologists to receive an ECG of the plurality of ECGs to allow receipt of a report for the ECG from the cardiologist before the requested review completion time; and
receiving a modification to the protocol data;
identifying at least one ECG from the plurality of ECGs to be reprocessed, wherein the identifying is based on the modification to the protocol data; and
reprocessing the at least one ECG identified from the plurality of ECGs, wherein reprocessing is in accordance with the modification to the protocol data.

8. The method of 7, wherein the modification to the protocol data comprises at least one of:
changing the protocol data for a first clinical trial to the protocol data for a second clinical trial; or
changing at least one of: the requested completion time; or a rule of the protocol rules.

9. The method of claim 7, wherein the processing comprises:
receiving the measurements of the ECG of the plurality of ECGs.

10. The method of claim 7, further comprising transmitting the report to at least one of a system or organization over a network.

11. The method of claim 7, further comprising:
performing an error check on the protocol data associated with the ECG; and
performing an error check on the ECG.

12. The method of claim 7, wherein determining the cardiologist among the plurality of cardiologists to receive the ECG of the plurality of ECGs is based on shift ending times for the plurality of cardiologists.

13. The method of claim 7, wherein identifying at least one ECG from the plurality of ECGs to be reprocessed by determining the modification to the protocol data requires a specified measurement not present in the measurement of the at least one ECG.

14. A computer program product comprising code stored on a computer-readable medium, the code comprising:
code for receiving a plurality of electrocardiograms (ECGs), each ECG being associated with protocol data, the protocol data comprising a requested review completion time and protocol rules;
code for receiving a representation of an amount of distributed ECGs present in each technician queue among a plurality of technician queues;
code for receiving a representation of an amount of distributed ECGs present in each cardiologist queue among a plurality of cardiologist queues;
code for processing the plurality of ECGs to receive measurements of the plurality of ECGs and to receive results of cardiologists reviewing the measurements, the code for processing comprising:
code for determining a technician among a plurality of technicians to receive an ECG of the plurality of ECGs based on the requested review completion time for the ECG and based on the representation of the amount of distributed ECGs present in each technician queue; and
code for determining a cardiologist among a plurality of cardiologists to receive for review an ECG of the plurality of ECGs and to receive a measurement associated with the ECG of the plurality of ECGs, based on the requested review completion time and based on the representation of the amount of distributed ECGs present in each cardiologist queue, to allow receipt of a report for the ECG from the cardiologist before the requested review completion time;

code for receiving a modification to the protocol data;

code for identifying, based on the modification to the protocol data, at least one ECG from the plurality of ECGs to be reprocessed; and code for reprocessing, in accordance with the modification to the protocol data, the at least one ECG identified from the plurality of ECGs.

15. The computer-readable medium of claim 14, wherein the modification to the protocol data comprises at least one of:

changing the protocol data for a first clinical trial to the protocol data for a second clinical trial; or changing at least one of: the requested completion time; or a rule of the protocol rules.

16. The computer-readable medium of claim 14, further comprising code for transmitting the report to at least one of a system or organization over a network.

17. The computer-readable medium of claim 14, further comprising:

code for performing an error check on the protocol data associated with the ECG; and code for performing an error check on the ECG.

18. The computer-readable medium of claim 14, wherein code for determining the cardiologist among the plurality of cardiologists to receive for review the ECG of the plurality of ECGs and to receive the measurement associated with the ECG of the plurality of ECGs comprises code for determining the cardiologist to receive the ECG and measurements based on shift ending times for the plurality of cardiologists.

19. The computer-readable medium of claim 14, wherein code for determining a technician among a plurality of technicians to receive an ECG of the plurality of ECGs comprises code for determining the technician to receive the ECG based on shift ending times for the plurality of cardiologists.

* * * * *